United States Patent [19]

Kronner

[11] Patent Number: 5,169,387
[45] Date of Patent: Dec. 8, 1992

[54] METHOD AND APPARATUS FOR CATHETERIZATION OF A BODY CAVITY

[76] Inventor: Richard F. Kronner, 1443 Upper Cleveland Rapids Rd., Roseburg, Oreg. 97470

[21] Appl. No.: 680,151

[22] Filed: Apr. 3, 1991

[51] Int. Cl.⁵ .......................................... A61M 31/00
[52] U.S. Cl. ...................................... 604/51; 604/164
[58] Field of Search .............. 604/51, 52, 53, 158, 604/161, 162, 163, 164, 165, 169, 170, 171; 128/763, 765

[56] References Cited

U.S. PATENT DOCUMENTS

| | | | |
|---|---|---|---|
| 3,633,579 | 1/1972 | Alley et al. | 604/165 |
| 4,677,978 | 7/1987 | Melker | 604/51 |
| 4,911,691 | 3/1990 | Aniuk | 604/164 |
| 4,978,334 | 12/1990 | Toye et al. | 604/51 |
| 4,986,814 | 1/1991 | Burney et al. | 604/164 |
| 5,019,039 | 5/1991 | Anderson | 604/51 |

Primary Examiner—Gene Mancene
Assistant Examiner—Michael Lynch
Attorney, Agent, or Firm—Kolisch, Hartwell, Dickinson, McCormack & Heuser

[57] ABSTRACT

A method and apparatus for catheterization of a body cavity, the catheterization apparatus having a sheath, a cannula with a blunt end and a stylet with a sharp end. To use the apparatus the three elements are initially arranged with the stylet leading the apparatus. The apparatus is advanced a distance into the flesh of a patient. The apparatus is readjusted leaving the cannula in a leading position. The apparatus is then advanced further into the flesh of the patient and into communication with a body cavity. The apparatus is again readjusted, leaving the sheath in communication with the body cavity.

6 Claims, 3 Drawing Sheets

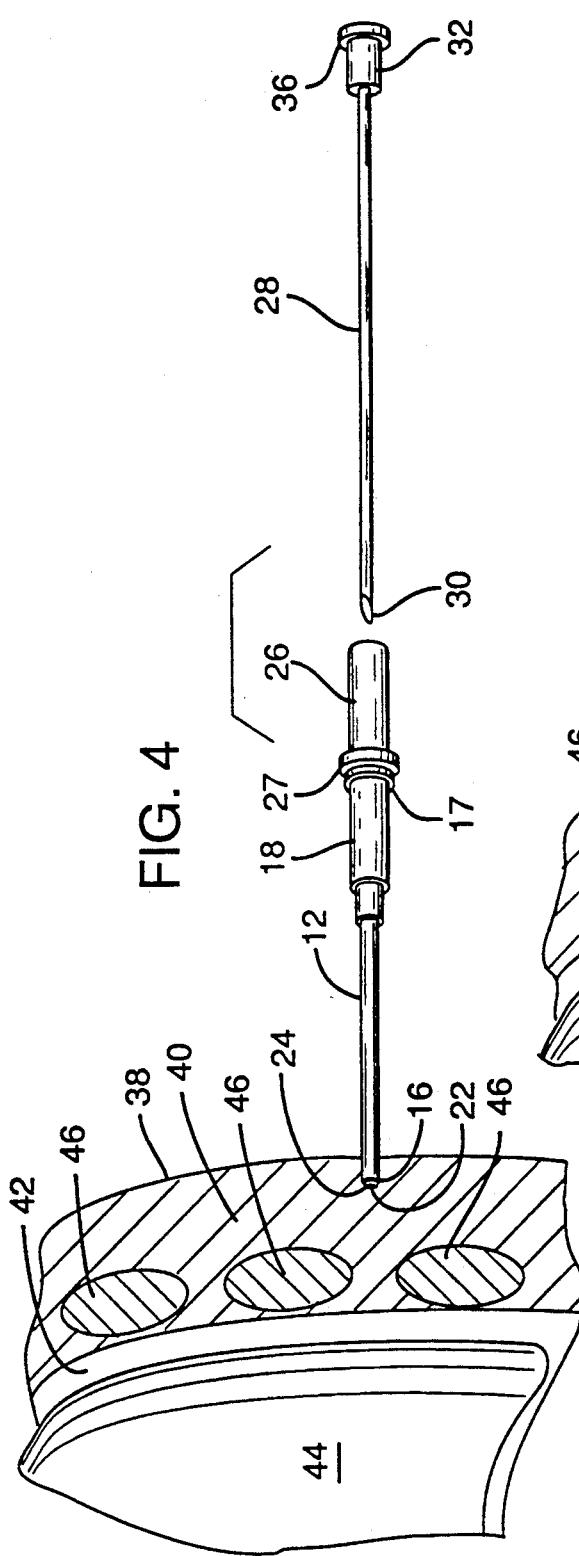
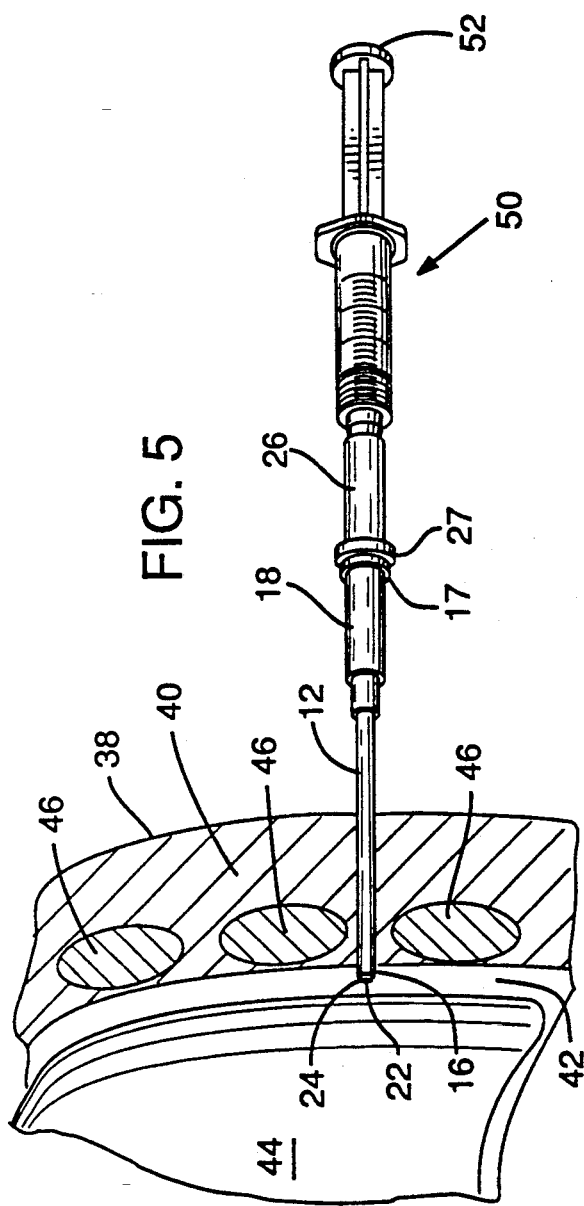

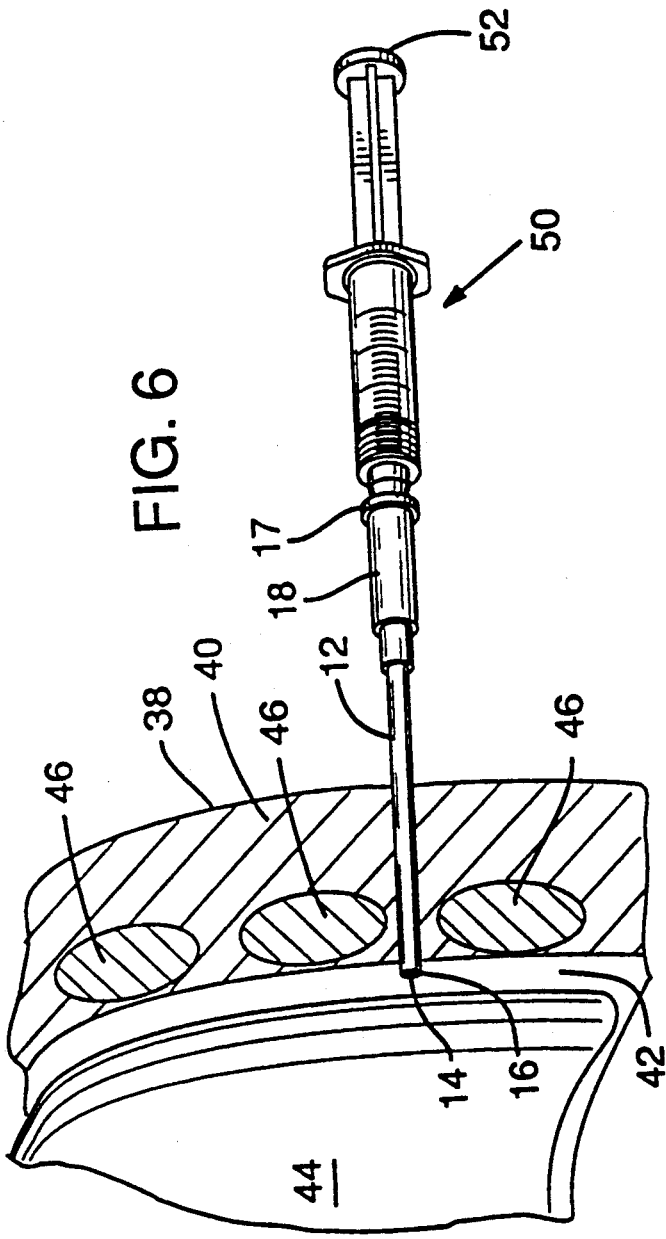

METHOD AND APPARATUS FOR CATHETERIZATION OF A BODY CAVITY

BACKGROUND OF THE INVENTION

1. Field of the Invention

This invention relates generally to a method and apparatus for the catheterization of a body cavity, and more particularly to a method and apparatus for the catheterization of a cavity between the lung and inner chest wall of a patient so that fluid may be drained therefrom.

2. Prior Art

When a patient suffers from tumors or infection involving the lungs, it is possible for fluid to collect in the chest cavity between the patient's lung and inner chest wall. Such a situation may lead to breathing difficulties, potentially endangering the patient's life. It is, therefore, common procedure to remove any such accumulated fluid, thereby improving the patient's ability to breath, and, upon analysis of the removed fluid, aiding in diagnosis of the patient's problem.

Removal of such fluid is generally accomplished using a catheter which is inserted through the patient's skin and flesh and into communication with the chest cavity. The fluid is then drained through the catheter. This procedure is known in the art as thoracentesis. Because it is a simple procedure, thoracentesis is often performed in a doctor's office, substantially decreasing the cost to the patient.

Insertion of the catheter, known in the art as catheterization, is commonly accomplished using an apparatus having a needle surrounded by a closely-fitting sheath. In previously known catheterization apparatus, it is necessary to insert both the needle and the sheath through the flesh and into communication with the patient's chest cavity. The needle acts as a relatively aggressive penetrator, carrying the sheath with it. After penetrating the chest cavity, the needle is removed, leaving only the sheath. The sheath thereafter provides a path allowing for fluid to be drained.

If the needle is inserted too far, however, a lung may be punctured, collapsing the lung and endangering the life of the patient. Such a situation may require insertion of a chest tube to evacuate air until the lung is sealed, and usually requires emergency medical care. Additionally, time in the hospital might be involved, substantially increasing the cost of treatment.

Accordingly, it is an object of the present invention to provide a safe method and apparatus for insertion of a catheter into a body cavity. More specifically, it is an object of this invention to provide a method and apparatus wherein the extent of penetration of the chest cavity can be safely determined.

SUMMARY OF THE INVENTION

The above object is achieved by the provision of a catheterization apparatus which includes a stylet having a sharp end, a cannula, and a sheath. The sheath has a sheath passageway which receives the cannula and the cannula has a cannula passageway which receives the stylet creating a consolidated apparatus.

To use the apparatus, it is arranged such that the stylet end leads the apparatus. The apparatus is then advanced through the skin and into the flesh of the patient. The stylet is then retracted, leaving the cannula in a position with an end thereof leading the apparatus. The apparatus is then further advanced through the flesh and either into the patient's chest cavity or to a position directly adjacent to the patient's chest cavity. The cannula is the removed and fluid is drained.

Further objects and advantages of the present invention will become more fully apparent upon a careful reading the following description in conjunction with the included drawings.

BRIEF DESCRIPTION OF THE DRAWINGS

FIG. 4 illustrates removal of the stylet from the catheterization apparatus.

FIG. 5 illustrates penetration into the chest cavity by the catheterization apparatus.

FIG. 6 illustrates drainage of the chest cavity using a syringe.

DETAILED DESCRIPTION OF THE PREFERRED EMBODIMENT

Figure 1:
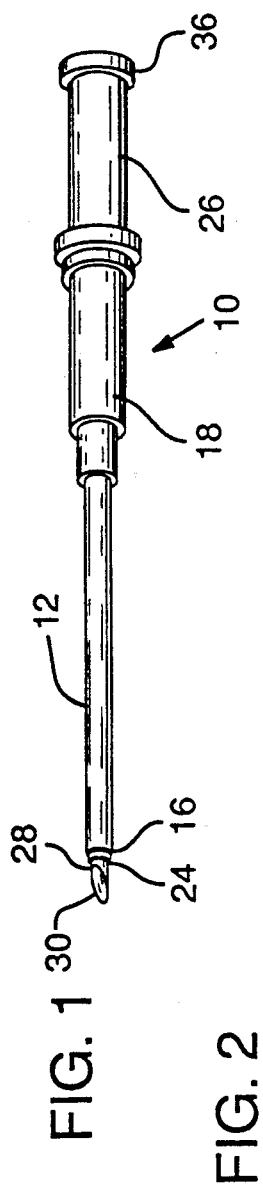
FIG. 1 is a perspective view showing the preferred embodiment of the catheterization apparatus of the present invention.
Figure 2:
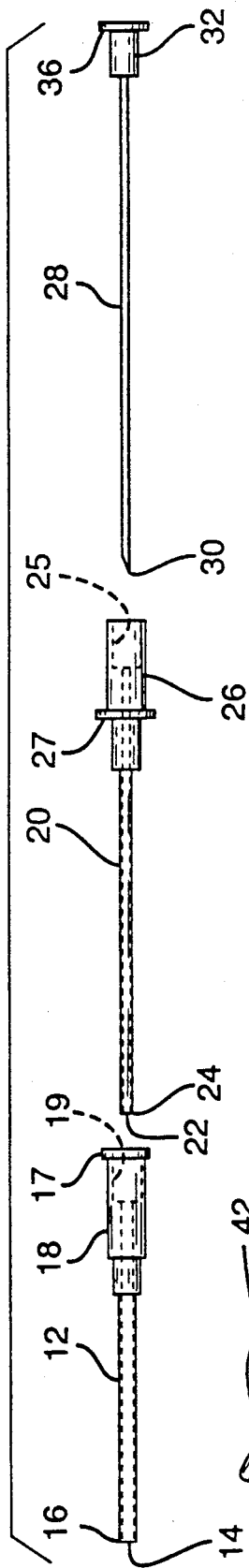
FIG. 2 is an exploded side view of the catheterization apparatus of FIG. 1.

A preferred embodiment of the invented catheterization apparatus has been depicted in the drawings and is generally indicated at 10 in FIG. 1. Although the invented catheterization apparatus may be used to access any body cavity, it is particularly adapted for use in thoracentesis catheterization.

The invented catheterization apparatus 10 includes an elongate sheath 12 having a sheath passageway 14. Sheath passageway 14 extends longitudinally along the entire length of sheath 12. Sheath 12 is a thin, tubular element having an outer diameter allowing for insertion through a patient's skin and flesh without seriously traumatizing the patient. To further reduce the risk of injury, sheath 12 preferably is composed of a flexible plastic material such as polyethylene. The sheath terminates at a blunt sheath end 16 (end 16, for instance, being slightly rounded). Sheath 12 may therefore remain in communication with the patient's chest cavity for extended periods of time without risking injuries because of patient movement.

Integral with sheath 12 is a hollow sheath hub 18 which terminates in a flange 17. Sheath hub 18 defines a cylindrical recess 19 which joins with passageway 14. Recess 19 may be used in mounting a syringe or other device.

Apparatus 10 also includes a cannula 20 having a cannula passageway 22. Cannula passageway 22 extends along the entire length of cannula 20. In the preferred embodiment cannula 20 is a tubular element having an outer diameter such that it may be inserted through sheath passageway 14 in close fitting arrangement. Cannula 20 may be composed of a rigid material, preferably a material such as stainless steel. Cannula 20 terminates at a blunt cannula end 24. Cannula end 24 provides cannula 20 with a penetrator which is aggressive enough to advance through the patient's flesh but is not aggressive enough to puncture an internal organ.

Integral with cannula 20 is a hollow cannula hub 26. Cannula hub 26 defines a recess 25 and terminates in a flange 27. Recess 25 enables a syrinqe or other suction device to be mounted on the cannula with suction producible by the suction device mounted on cannula passageway 22. Flange 27 engages flange 19 to limit the extent which cannula 20 may be inserted through sheath passageway 14. With the cannula fully inserted, cannula end 24 extends beyond sheath end 16.

A stylet 28 is also an element of apparatus 10. Stylet 28 is an elongate element having an outer diameter such that it may be inserted through cannula passageway 22 in close-fitting relationship. In the preferred embodiment, stylet 28 is composed of a rigid material such as stainless steel and terminates at a sharp stylet end 30. Stylet 28 is thereby provided with relatively aggressive penetrator, able to puncture the skin of the patient.

A stylet hub 32 is mounted to the stylet, providing a region 34 which may be engaged by the fingers of a technician to advance apparatus 10 into the chest of the patient. Stylet hub 32 terminates in a flange 36 which engages cannula hub 26 to limit the extent which stylet 28 may be inserted through cannula passageway 22. With flange 36 against hub 26, end 30 of the stylet projects beyond end 24 of the cannula.

Method of Operation

Access of an internal body cavity using the catheterization apparatus is accomplished as illustrated in FIGS. 3 through 6. Apparatus 10 is shown puncturing a patient's skin 38. The apparatus then penetrates the patient's flesh 40, passing the patient's ribs 46, and entering the patient's chest cavity 42. Penetration of the apparatus is discontinued prior to puncture of the patient's lung 44.

Figure 3:
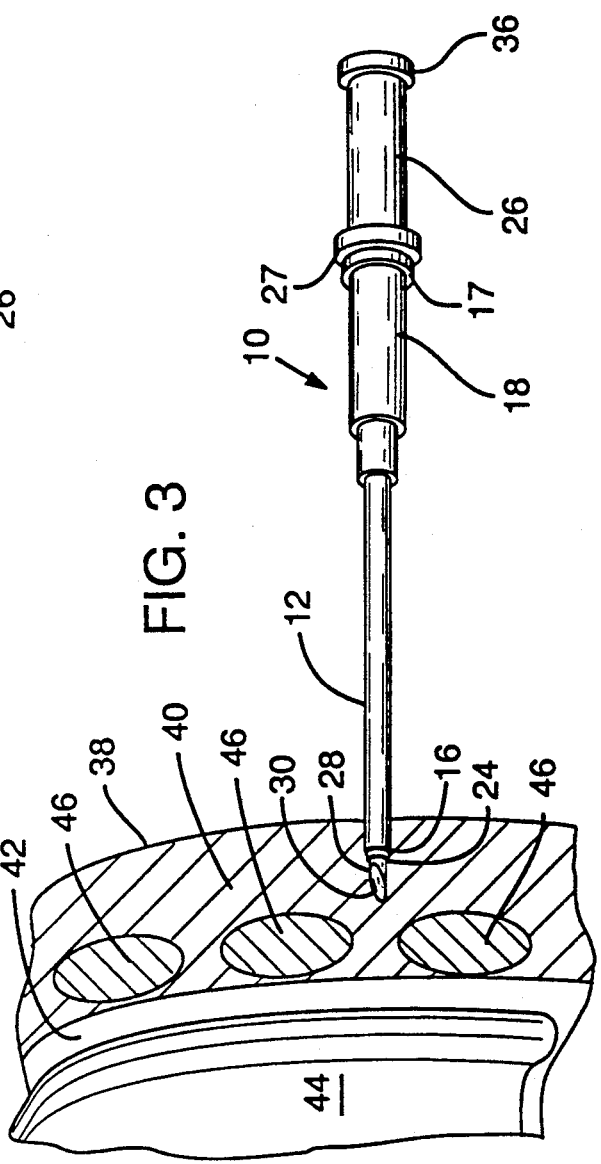
FIG. 3 illustrates the puncture of the patient's skin with the catheterization apparatus.

Referring first to FIG. 3, apparatus 10 is shown with sheath 12 receiving cannula 20 and cannula 20 receiving stylet 28. Stylet end 30 leads apparatus 10, providing a first relatively aggressive penetrator. While in this arrangement, apparatus 10 is used to puncture the patient's skin, the apparatus being inserted a short distance into the patient's flesh. The distance which the apparatus is inserted into the patient's flesh is less than the distance between the skin and the chest cavity. The proper distance to the insert apparatus is indicated when the apparatus begins to advance with greater ease. This indicates advancing through the patient's flesh.

After the skin has been punctured, apparatus 10 is adjusted by retracting stylet 28. As shown in FIG. 4, stylet 28 may be completely removed leaving cannula passageway 22 unobstructed. Upon retracting stylet 28, cannula end 24 is left in a position leading apparatus 10. This provides apparatus 10 with a second less aggressive penetrator as compared to stylet end 30. Although cannula end 24 will penetrate the tissue between the skin and the chest cavity, it will not puncture the lung.

After retracting stylet 28, a syringe 50 is coupled to cannula hub 26. Syringe 50 is preferably made of a transparent or semi-transparent plastic enabling the technician to see fluid entering the syringe. By pulling back on the syringe plunger 52, suction may be applied through cannula passageway 22. While suction is applied through cannula passageway 22, apparatus 10 is advanced through the flesh and into the chest cavity of the patient. Penetration into the chest cavity is indicated when syringe 50 produces fluid as shown in FIG. 5.

After penetrating the chest cavity, apparatus 10 is readjusted by retracting cannula 20. Cannula 20 may be completely removed from sheath passageway 14 leaving only sheath 12 in communication with the chest cavity.

Fluid may then be drained from the chest cavity by applying suction through sheath passageway 14 using a syringe as shown in FIG. 6.

Although a preferred embodiment and method of the invention have been disclosed, it should be appreciated that variations and modifications may be made without departing from the scope of the invention as defined by the claims.

I claim:

1. A catherization apparatus comprising:
    an elongate flexible plastic sheath having a sheath passageway extending therealong, said sheath terminating at a blunt sheath end and having an opposite end;
    a sheath hub joined to said opposite end of said elongate sheath;
    an elongate stiff cannula having a cannula passageway extending along the length of the cannula, said cannula being removably received within said sheath passageway and terminating at a flesh-piercing cannula end, said cannula end extending a predetermined distance beyond said sheath end, said cannula having an end opposite the flesh-piercing end of the cannula;
    a cannula hub joined to said opposite end of said cannula, said cannula hub engaging said sheath hub to limit extension of said cannula end beyond said predetermined distance beyond said sheath end;
    an elongate stiff stylet removably received within said cannula passageway and the stylet terminating at a sharp skin-piercing stylet end, said stylet end extending a predetermined distance beyond said flesh-piercing cannula end, said stylet having and end opposite said skin-piercing stylet end; and
    a stylet hub joined to said end of said stylet opposite said skin-piercing end, said stylet hub engaging said cannula hub to limit extension of said skin-piercing stylet end beyond said predetermined distance beyond said flesh-piercing cannula end.

2. The apparatus of claim 1, and further comprising a syringe with barrel and connecting needle, and the syringe being removably mountable on the cannula with the syringe needle in the cannula passageway and the syringe barrel against the cannula hub and the end of the needle covered by the cannula.

3. A thoracentesis method of accessing and removing fluid from a chest cavity at least partially bounded by a flesh layer, the method comprising:
    providing a thoracentesis apparatus comprising a hollow flexible plastic sheath, and a first rigid elongate flesh-piercing adjustable penetrator and a second rigid elongate flesh-piercing adjustable penetrator, the second penetrator extending along the interior of the sheath and the first penetrator extending along a passage in the second penetrator and the first penetrator having a more aggressive piercing action than the second penetrator;
    adjusting the apparatus so that the first penetrator extends beyond the end of the sheath and leads the assembly;
    with a piercing cut piercing the flesh layer to advance the apparatus into but only partially through the flesh layer with the first penetrator piercing the layer and leading the advance;
    readjusting the apparatus so that the second penetrator replaces the first penetrator as the penetrator that extends beyond the end of the sheath and leads the apparatus;

further piercing the flesh layer to advance the apparatus into the flesh layer with the second penetrator piercing the layer and leading the advance until a position adjacent the cavity is reached; and again readjusting the apparatus to leave the sheath leading the apparatus and extending into the cavity.

4. The method of claim 3, wherein the first-mentioned readjustment is done with retracting of the first penetrator to leave a passageway extending along the apparatus, a suction is then applied to the passageway, and the apparatus is then further advanced until fluid is removed by the suction to indicate that the cavity is reached.

5. A thoracentesis method of accessing and removing fluid from a chest cavity where the chest cavity is at least partially bounded by a flesh layer, the method comprising:

providing a thoracentesis apparatus with a first relatively aggressive penetrating capability;

initially with a piercing cut piercing the flesh layer to advance the apparatus partially into but not through the flesh layer using the first relatively aggressive capability;

providing the apparatus with a second less-aggressive penetrating capability;

further with a piercing cut piercing the flesh layer to advance the apparatus into the flesh layer to place the apparatus in communication with the chest cavity using the second less-aggressive penetrating capability; and having placed the apparatus in communication with the chest cavity, removing fluid from the chest cavity.

6. The method of claim 5, wherein after initial piercing and prior to the further piercing, a passageway extending along the apparatus is established, and while further piercing to advance the apparatus into the flesh layer, a suction is applied to the passageway to remove fluid which may be encountered.

* * * * *